(12) United States Patent
Pasula

(10) Patent No.: US 9,005,915 B2
(45) Date of Patent: Apr. 14, 2015

(54) METHOD FOR IN VITRO BLOOD TESTING

(75) Inventor: Mark J. Pasula, Palm Beach Gardens, FL (US)

(73) Assignee: Oxford Biomedical Technologies, Inc., Riviera Beach, FL (US)

(*) Notice: Subject to any disclaimer, the term of this patent is extended or adjusted under 35 U.S.C. 154(b) by 663 days.

(21) Appl. No.: 12/755,179

(22) Filed: Apr. 6, 2010

(65) Prior Publication Data

US 2011/0244505 A1    Oct. 6, 2011

(51) Int. Cl.
 *C12Q 1/02* (2006.01)
 *G01N 33/569* (2006.01)

(52) U.S. Cl.
 CPC ............... *G01N 33/56972* (2013.01)

(58) Field of Classification Search
 CPC .............................. G01N 33/56972
 See application file for complete search history.

(56) References Cited

U.S. PATENT DOCUMENTS

| | | | |
|---|---|---|---|
| 4,528,274 A * | 7/1985 | Carter et al. | 436/10 |
| 4,614,722 A | 9/1986 | Pasula | |
| 4,788,155 A | 11/1988 | Pasula | |
| 4,882,284 A | 11/1989 | Kirchanski et al. | |
| 5,147,785 A | 9/1992 | Pasula | |
| 6,114,174 A | 9/2000 | Pasula | |
| 6,200,815 B1 | 3/2001 | Pasula | |
| 6,232,125 B1 * | 5/2001 | Deka et al. | 436/63 |
| 7,256,048 B2 * | 8/2007 | Simon-Lopez | 436/63 |

* cited by examiner

*Primary Examiner* — Robert Yamasaki
(74) *Attorney, Agent, or Firm* — The Law Offices of Roger S. Thompson

(57) ABSTRACT

Method for determining the presence of a malady in a patient by measuring the degree of reaction of individual types of white blood cells (basophils, eosinophils, neutrophils, monocytes and lymphocytes) in the patient's blood. The degree of reaction of each type of white blood cells is determined by comparing the volumetric size distributions of the types of white blood cells before and after exposure to suspected reactants. Positive results of a change in the volumetric size distribution of the individual types of white blood cells in response to exposure to a specific reactant indicates the presence of a specific malady, such as an allergic reaction to the suspected reactant.

21 Claims, 4 Drawing Sheets

METHOD FOR IN VITRO BLOOD TESTING

BACKGROUND OF THE INVENTION

1. Field of the Invention

This invention is directed to the field of in vitro blood testing and, more particularly, to in vitro blood testing for determining the presence of a reaction in a patient's blood which would indicate whether the patient has a malady, such as an allergy, adverse reactions, sensitivity etc.

2. Description of the Related Art

Blood tests for diagnosing whether a patient is suffering from any of a variety of maladies have been around for many years. For example, cytotoxic testing and scratch testing have been used to determine whether an individual is sensitive to suspected allergens. These tests had many drawbacks. In vivo tests, such as scratch testing, involved exposing living subjects to potentially hazardous allergens. Known in vitro diagnostic testing could also be unreliable and inconsistently reproducible.

Beginning in the 1980's, the inventor herein began to develop more consistently repeatable methods for in vitro testing for food sensitivities and other maladies whose presence could be indicated by reactions with blood cells. For example, the inventor's own prior U.S. Pat. Nos. 4,614,722; 4,788,155; 5,147,785; 6,114,174; and 6,200,815, the disclosures of which are herein incorporated by reference as though set forth in full, disclose various methods of in vitro diagnostic blood tests.

Generally speaking, these patents are directed to methods and apparatus for detecting, measuring and evaluating responses of a patient's blood cells to exposure to potential reactants, such as suspected allergens, or other substances which could cause immune and/or none immune reactions. The inventor's prior work was based on his determination that blood cells (usually white blood cells, "wbcs", but also red blood cells, "rbcs", or platelets) react when in the presence of certain reactants. For example, when an individual is allergic to a particular food, if that individual's blood is exposed to that food, the blood reacts as though invaded by an infection—the blood cells may expand, release histamines, engulf the reactant or otherwise change size, including completely lysing, i.e., releasing of the cell's contents. By measuring the degree of size changes of the white blood cells, the nature and degree of reaction can be determined. The inventor's prior methods involved taking a sample of the patient's blood, and separating it into equal alequats of samples. One sample is not exposed to the potential reactants, or allergens, and that sample is used as a control sample. The other samples are exposed to differing potential reactants, or groups of reactants, and the cell counts of the control and test samples are compared to see if the test samples have different size distributions of blood cells than does the control sample.

But there are problems associated with the inventor's prior tests.

First, the blood cells that are the most sensitive to these type of reactions are the white blood cells. As described in the inventor's earlier work, and as is widely known, white blood cells and red blood cells are generally the same size, and red blood cells vastly outnumber white blood cells (by a multiple on the order of 500:1), so that attempts to measure reactions solely of the white blood cells in the presence of red blood cells is virtually impossible. The overwhelming number of red blood cells compared to white blood cells obscures any attempt to count white blood cells alone.

This problem is addressed in the inventor's prior work by lysing, i.e., destroying, the red blood cells by introducing a lysing agent into a sample of the patient's blood. After the red blood cells are lysed, the white blood cells may be counted. This leads to a different problem, however, since the same lysing agent that lyses red blood cells usually lyses white blood cells, as well, albeit more slowly.

Second, the inventor has now determined that different types of white blood cells exhibit different reactions to reactants, and that measuring the direction and degree of reactions of different types of white bloods may provide better information to permit more precise diagnoses for the patient. In prior testing, this pattern was not recognized, so that an increase in one type of white blood cell (e.g., monocytes) could mask a decrease in another type of white blood cell (e.g., eosinophils), so that the overall measurement could indicate no change in the overall size or distribution of white blood cells, while there were actually two different and complementary reactions, resulting in a false negative.

SUMMARY OF THE INVENTION

There is thus a need in the art to provide an improved method and apparatus for diagnosing allergies and other maladies through an improved in vitro blood test.

It is therefore an object of the invention to provide an improved in vitro blood test, in which blood test the reactions, if any, of the subject's white blood cells are determined by measurement of any size change of the different types of white blood cells after lysis of the subject's red blood cells.

It is a further object of the invention to provide an improved in vitro blood test for diagnosing maladies in a subject by measuring the size distribution of specific types of white blood cells before and after exposure to a suspected reactant, wherein size shifts of the distribution of different types of white blood cells indicate positive diagnoses.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1:
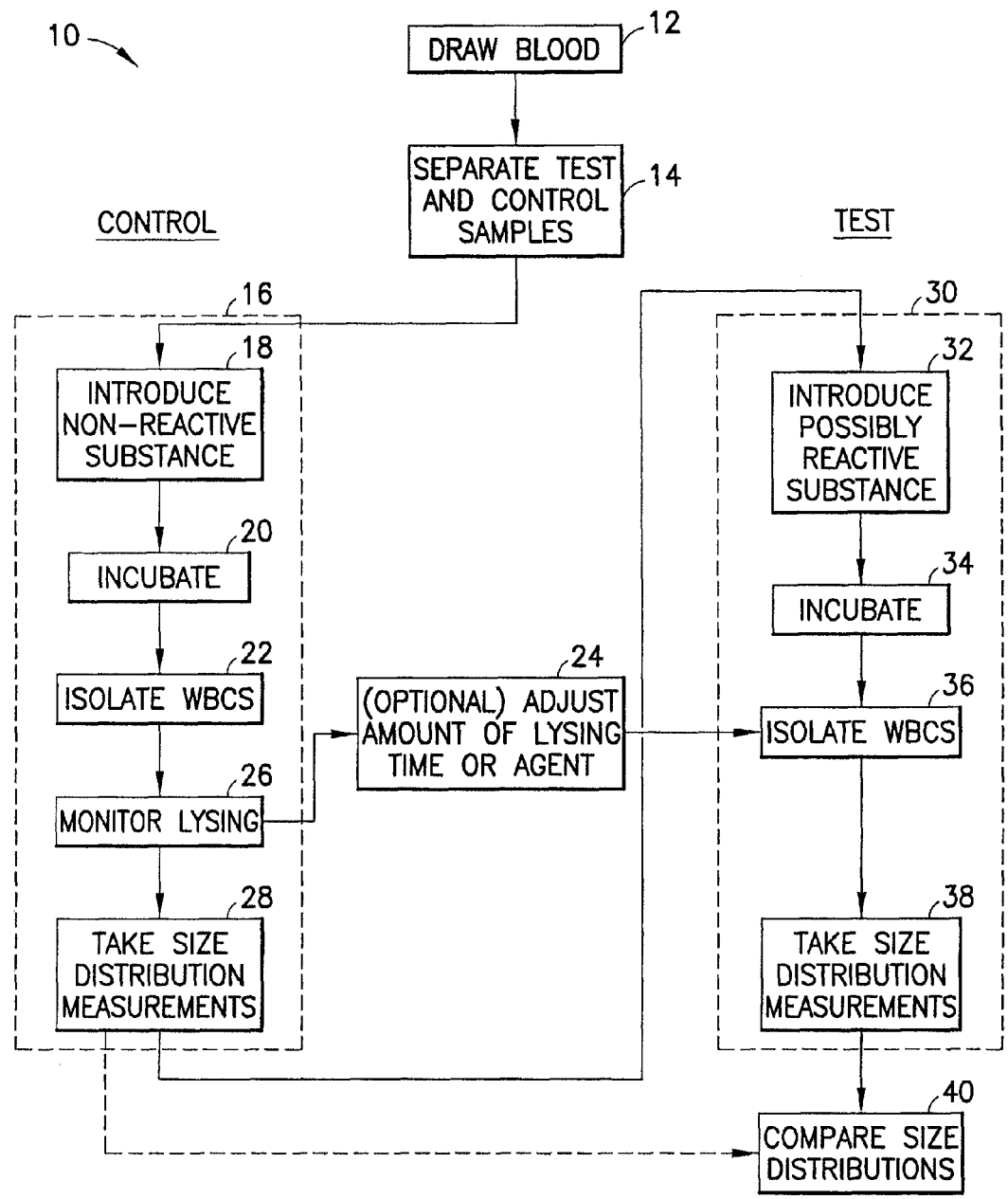
FIG. 1 is a flow chart showing the practice of the inventive method.

The inventive method may be best understood by reference to FIG. 1, which illustrates a simplified flow chart thereof. The method is shown generally at 10. To begin, a patient who is suspected of having a malady has a sample of his or her blood drawn (12). The sample must be large enough to be divided into smaller samples to be used as at least one control sample and at least one test sample (14). The number of test samples to be utilized depends upon the number of different tests to be run in the performance of the method. In the most preferred method, each test sample may be used for a single suspected reactant, and a panel of up to 50 or more samples may be run simultaneously. In other embodiments, it may be possible to have each test sample be used for more than one suspected reactant, so that more samples may be run at once, on the assumption that most suspected reactants will test negative. If a test sample with multiple reactants tests positive for a reaction (as will be described presently), then a second test can be run on the individual suspected reactants that were contained in the positive-testing test sample, for a final diagnosis.

In some preferred embodiments, the test samples are placed into a tray with 96 micro-wells, which would include micro-wells for the control samples, as well, so 91 to 94 individual test samples may be used, whether individual tests or small groups of tests. Other embodiments may utilize trays of different sizes, such as 48 or 52, depending upon the needs of the user. One of ordinary skill would be able to select an appropriate size and type of tray suitable for a desired application without undue experimentation. The test samples are preferably placed in wells that have been first coated with a non-reactive coating agent, and then a dry reactant, such as a suspected allergen is deposited in the well. For purposes of discussion, the suspected reactants will be described as potential allergens, as the inventive test is of particularly use in testing for food allergies, but this description should not be considered as being limited in applicability to testing for allergies, as, has been described in my earlier patents, the generally methodology has broader utility.

It should be noted that, when discussing the distribution of blood into the micro-wells, the blood is preferably whole blood, and is not diluted or otherwise different from what is found in the patient in vivo. One of ordinary skill in the art may find dilution of the blood to be useful in some applications, but that is not relevant to the present invention.

The number of test samples drawn should be sufficient to accommodate the number of tests to be performed, and one of ordinary skill in the art will be able to determine the appropriate amount of blood to be drawn to do so without undue experimentation. Currently, it is preferred to draw approximately 25-100 μl of blood for each well to be filled (whether for control or test samples). It is always preferred to draw the minimum amount of blood necessary from the patient to permit the proper testing, and so one of ordinary skill in the art should determine the amount of blood to be drawn with this limitation in mind.

For the tests to be performed with satisfactory confidence, the distribution of cells, white and red, in each sample should be approximately the same. This may preferably be accomplished by stirring, in any desired fashion, the larger sample, so that the smaller samples may be presumed to be substantially identical in content and distribution. For purposes of the invention, the uniformity of distribution of the blood cells is important, as the test, as will be described, will measure the (volumetric) size distributions of the various types of white blood cells: basophils, eosinophils, neutrophils, monocytes and lymphocytes. For accuracy, comparisons must be based upon starting samples (control and test) that have substantially the same size distributions.

After the test and control samples are separated (14), the control sample is prepared (16). It is noted, here, that for ease of discussion, the preparation of the test and control samples are described as being prepared and acted upon in series, first the control sample and then the test sample. In many embodiments, however, including the preferred embodiment, the test and control samples are processed essentially simultaneously, to speed the evaluation process.

First, with respect to the control sample, a non-reactive substance is introduced into the micro-wells (18) before placement of the blood therein, so that the content of the control well will be as similar as possible to the content of the test wells. The control sample is allowed to incubate (20) for an appropriate time. Usually from about 1.5 hours to about 2 hours is sufficient, although some applications will require incubation for longer or shorter times, possibly up to two or more days. One of ordinary skill in the art would be able to select an appropriate time for incubation, depending upon the known or determinable reaction times for the suspected reactant.

After incubation, the white blood cells will have had the opportunity to react, and so the testing may commence. As has been described in my earlier patents, when a measurement of white blood cells is to be made, it is necessary to separate the white blood cells from the red blood cells in the mixture, because red blood cells are generally of the same size as white blood cells, but greatly outnumber white blood cells (by a factor of about 500:1). One preferred way to remove red blood cells from the samples is by "lysis" (22), i.e., a chemical process which causes the red blood cells to burst and disappear from the blood. This is accomplished by introducing a lysing agent to the mixture. A preferred lysing agent is saponin. It will be appreciated that other methods of separating the white blood cells from the red blood cells are possible, including mechanical methods, and so the term "lysis" is here used as a generic term to mean the removal of red blood cells from the blood mixture by any appropriate means, and not be limited to the introduction of a lysing agent to the blood.

One potential problem arises in the use of a lysing agent, however. Many lysing agents, including saponin, work quickly on red blood cells, but also work on white blood cells, albeit much more slowly. Furthermore, the reactions of individuals to lysing agents can vary within fairly wide ranges, so that the reaction time of one patient may be much longer (or shorter) than that of another.

This means that it may be appropriate, although not required, to vary the timing of the inventive method's measurements in accommodation of the individual's reaction to the lysing agent. When performing the inventive method, it is useful to find the "sweet spot" (a non-reacting window) for the measurement of the reaction of the white blood cells when there are no further red blood cells to interfere with and confuse the measurements. It may therefore be preferred to determine the beginning and end of that interval after an individual's red blood cells are completely lysed, and before that individual's white blood cells begin to react to the lysing agent (24). This may be determined by use of the control sample, or one of several control samples. In this (optional) step (24), the optimal length of time to allow for lysing may be determined.

This step is considered optional (although still preferred) because experience teaches that most people have reaction times that fall within an "average" range, and the test may be performed under the assumption that an individual patient's reaction time is within the "average" range, and proceed accordingly. This speeds the performance of the testing which, in some instances, may be an important consideration. If the results of a specific patient's measurements are considered suspect by use of the "average" range, the test may simply be re-performed, with the additional use of the additional fine tuning step (24) to be described.

A suitable "average" range would be from about 1.5 mins. to about 3.5 mins. after introduction of the lysing agent.

According to this step (24), the control sample is observed (26) after introduction of the lysing agent, to determine when the count of red blood cells falls below a predetermined level. That moment in time is identified by observing the red blood cells. Monitoring of the control sample (26) continues to determine that point in time when lysis of the white blood cells commences, identifying a second point in time. This means that the measurement to be performed of the test sample must be performed within the range of time staring at the first identified point in time and concluding at the second identified point in time. It would be preferred if the measurement of the reactions of the test sample were to be performed at or close to the midpoint between those two points in time, but the practicalities of measurements, such as the fact that the measurements of the volumetric size distributions of the types of white blood cells are not taken instantaneously but must be taken over a short period of time and that measurements must be made of several different test samples, demand that some flexibility about the "sweet spot" be kept in mind. To accommodate these practicalities, it is preferred that the measurement of the types of white blood cells be performed between about one-third and about two-thirds of the length of the interval.

In some circumstances, where an individual's reactions times are far off the "norm", it may be useful to adjust the amount of lysing agent introduced to the samples, to lengthen or shorten the interval to place it within a practical window. One of ordinary skill in the art would appreciate the ease of varying the amount of lysing agent introduced to the test and control samples to adjust the lysing time to accommodate an individual's reaction times. If this is done, then it is preferred that a second (or, if necessary, further) control run be performed (not shown separately in FIG. 1) to ensure that the test is being performed reliably.

Once the user is satisfied that the measurement timing is suitable for the application (whether by pursuing optional step (24) or by use of the "average" time), then the volumetric size distributions of the different types of white blood cells are taken (28). In the preferred embodiment, the measurements are taken with a laser flow cytometer, such as a Beckman Coulter Hematology Flow Cytometer, having the capability of performing either impedance measurements or, more preferably, my ribbon MRT volumetric measuring method (described in my earlier U.S. Pat. No. 6,114,174). In this fashion, the laser splits wbcs into separate lymphocyte, monocyte, basophil, neutrophil and eosinophil fractions. The impedance method more accurately measures the volumes of each wbc fraction.

The various types of white blood cells may be differentiated by any method, such as staining and observing them under a blue laser light. Various methods for differentiation are described in U.S. Pat. No. 4,882,284, and the patents cited therein, the disclosures of all of which are hereby incorporated by reference.

The measurement of the size distributions of the white blood cells in the test sample(s) (30) generally follows the same procedure as for the control sample, thus ensuring the comparability of the two measurements. First, the blood is exposed to at least one possibly reactive substance (32). The volume and makeup of the possibly reactive substance should match as closely the non-reactive substance introduced to the control sample in step (18), again, for comparability with the results of the measurements of the control sample. The possibly reactive substances may be, for example, dried food extracts of suspected food allergens, if testing for food sensitivities. Other potential reactants may be used, as described in my prior patents.

After introduction of the potential reactant to the blood in the test sample, it is allowed to incubate (34) for the same amount of time and under the same conditions as the control sample, allowing for any alteration thereof as provided by optional step (24), after which the red blood cells are separated from the white blood cells (36). While any method of separation may be used, it is preferred that the same method of separation be performed on both the control sample and each test sample. After the separation, the size distributions of the different types of white blood cells present in the test sample are measured (38) and the results are compared. If the measurements determine that there is any statistically significant difference between the two sets of measurement of any single type of white blood cells, then there is a determination that the test sample has shown a positive reaction, and sensitivity to the suspected reactive substance is diagnosed. In this context, "statistically significant" means that the difference is at least as great as the error factor of the equipment (which is known for each piece of equipment used).

Figure 2A:
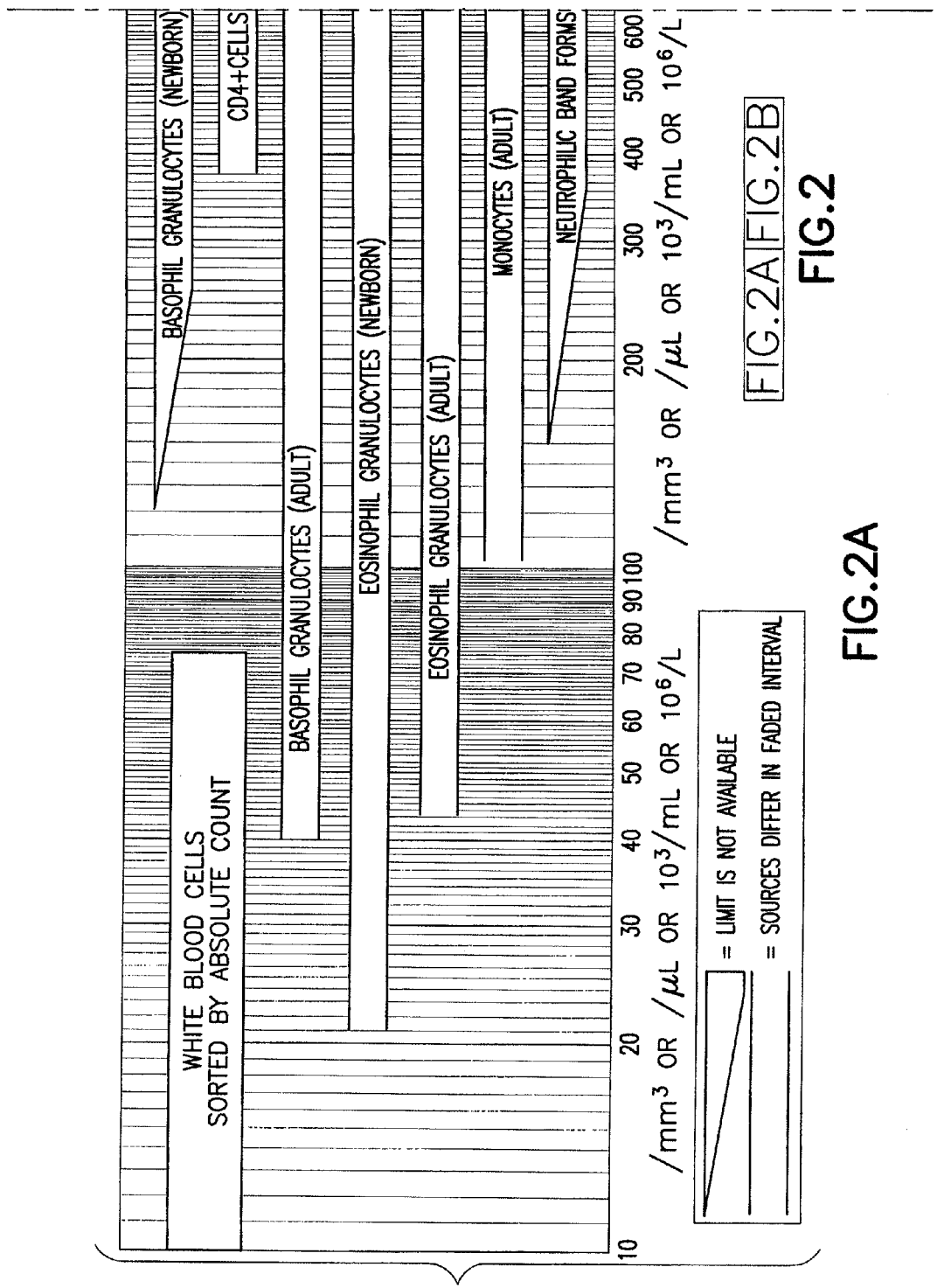
FIG. 2 is a volumetric size distribution chart of the various types of white blood cells.
Figure 2B:
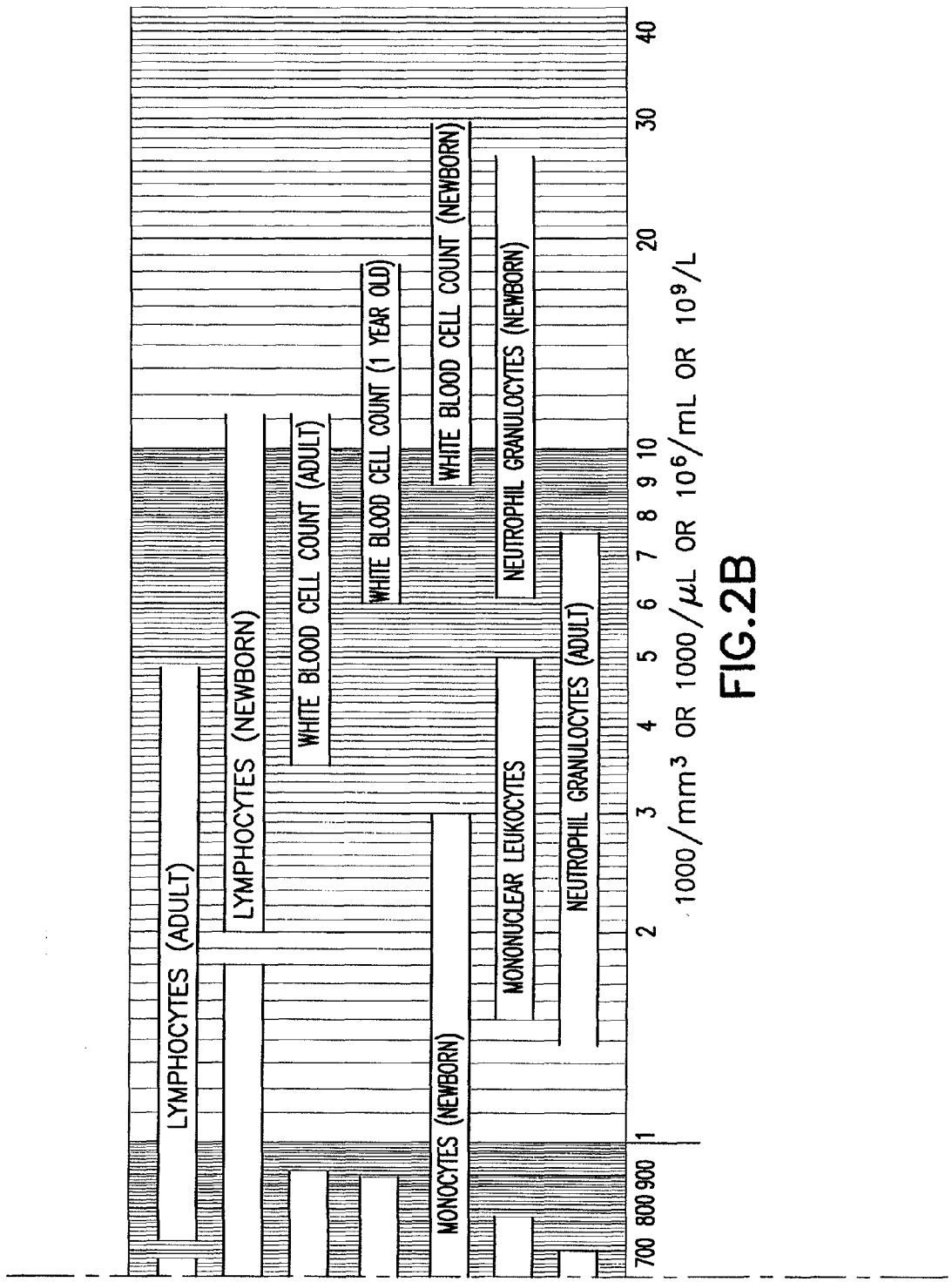
Figure 3:
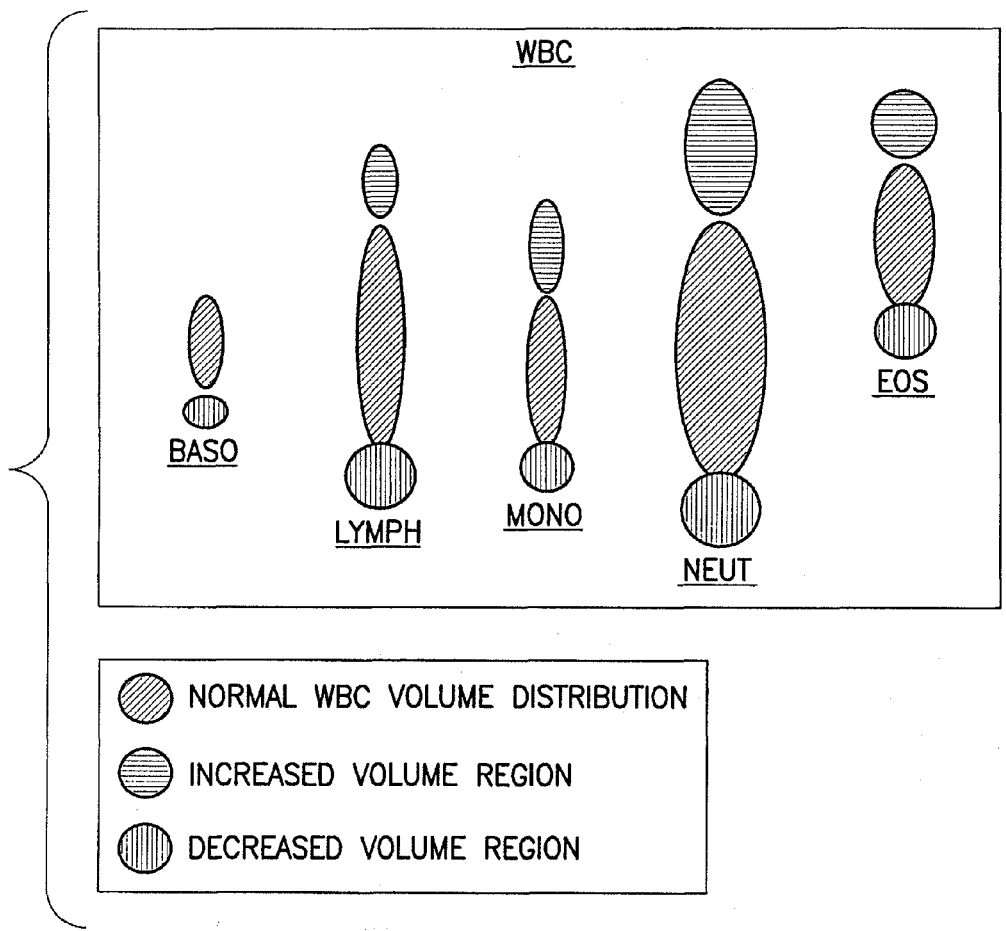
FIG. 3 is a stylized depiction (not to scale) of the possible variations in volumetric size distributions of each type of blood cell in response to exposure to a reactant, showing the possible changes which may take place if the patient is reactive to the reactant.

The inventive method is quite similar to those of my prior patented methods (other than the description of the measurement of lysing times). The difference, however, here, is the use of measurements of the changes in size of individual types of blood cells, and whether an individual type of blood cell has grown in size or diminished in size in response to the reactant. Previous methods did not differentiate between the various types of white blood cells, and so only the gross measurement of all white blood cells (for example) was used. However, this masked many types of positive reactions. For example, a reaction which only causes a change in the size of basophils may not be noticed, since basophils only make up a very small percentage of the total number of white blood cells, in the range of from about 0.3% to about 2% of all wbcs (see FIG. 2, a chart showing the relative distributions of the various types of unreacted white blood cells). A significant change in the size distribution of such cells would be completely lost and ignored as too small to matter if only the gross measurement of the total number of white blood cells is used. Also, a significant enlargement of monocytes could be masked if paired with a significant shrinkage in the size of eosinophils, and be recorded as a false negative, even though there are actually two positive reactions. Please see FIG. 3 for a chart showing the possible reactions of each type of white blood cell. Thus, the inventive method is capable of far more accurate diagnosis and detection of positive reactions than has heretofore been obtainable.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve substantially the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for diagnosing whether a subject is sensitive to a reactant associated with a specific malady, the method comprising the steps of:
   separating a sample of the subject's blood having at least first and second types of white blood cells into a control sample and at least one test sample, each of said control sample and said at least one test sample having a distribution of said at least first and second types of white blood cells substantially equal to that of said sample;
   determining size distributions for each of said first and second types of white blood cells in said control sample;
   introducing a suspected reactant, associated with a specific malady, to said at least one test sample;
   determining size distributions for each of said first and second types of white blood cells in said at least one test sample after introduction thereinto of said suspected reactant;
   comparing said size distribution of at least one of said first and second types of white blood cells from said at least one test sample with said size distribution of said at least one of said first and second types of white blood cells from said control sample; and
   determining a positive diagnosis where the results of said comparison indicates a difference in said size distribution of said at least one type of white blood cell in said control sample and in said at least one test sample by more than a predetermined amount.

2. The method of claim 1, wherein said step of determining said size distributions of each of said first and second types of white blood cells is performed within a predetermined range of time after introduction of said suspected reactant into said at least one test sample.

3. The method of claim 1, wherein said first and second types of white blood cells are selected from the group consisting of: basophils, eosinophils, neutrophils, monocytes and lymphocytes.

4. The method of claim 1, further comprising the steps of:
   comparing said size distribution of said first type of white blood cells from said at least one test sample with said size distribution of said first type of white blood cells from said control sample;
   comparing said size distribution of said second type of white blood cells from said at least one test sample with said size distribution of said second type of white blood cells from said control sample; and
   determining the existence of a positive diagnosis where the results of at least one of said comparisons indicates a difference in said size distribution of least one type of white blood cell in said control sample from said size distribution of that type of white blood cell in said at least one test sample by more than a predetermined amount.

5. The method of claim 1, wherein at least first and second suspected reactants are introduced into a test sample; and said method further comprises the steps of:
   separating out respective first and second individual test samples of said sample of said subject's blood;
   introducing said first suspected reactant, associated with a specific first malady, to said first individual test sample;
   introducing said second suspected reactant, associated with a specific second malady, to said second individual test sample;
   introducing a lysing agent to said first and second individual test samples;
   determining size distributions for each of said first and second types of white blood cells in said first individual test sample after a first point in time and before a second point in time;
   determining size distributions for each of said first and second types of white blood cells in said second individual test sample after said first point in time and before said second point in time;
   comparing said size distribution of at least one of said first and second types of white blood cells from said first individual test sample with said size distribution of said at least one of said first and second types of white blood cells from said control sample;
   comparing said size distribution of at least one of said first and second types of white blood cells from said second individual test sample with said size distribution of said at least one of said first and second types of white blood cells from said control sample;
   determining a positive diagnosis where the results of said comparisons indicate a difference in said size distribution of said at least one type of white blood cell in said control sample and in said first individual test sample; and
   determining a positive diagnosis where the results of said comparisons indicate a difference in said size distribution of said at least one type of white blood cell in said control sample and in said second individual test sample.

6. The method of claim 5, wherein said control sample includes at least first and second control samples;
   wherein said lysing agent is introduced into said first control sample, and wherein said method further comprises the steps of:
      determining said first and second points in time, wherein said first point in time is a point at which the lysis of red blood cells in said first control sample has reached a predetermined point and the second point in time is a point at which at least one of said first and second types of white blood cells in said first control sample have begun to change in volume; and
   determining said size distributions of said first and second types of white blood cells in said second control sample.

7. The method of claim 6, wherein the method further comprises the steps of:
   after determining said first and second points in time, adjusting an amount of said lysing agent to be introduced into said at least one test sample;
   estimating an adjusted first point in time at which it is estimated that lysis of said red blood cells will be completed in said test sample based upon said adjustment of said amount of said lysing agent;
   estimating an adjusted second point in time at which it is estimated that at least one of said first and second types of white blood cells in said control sample begins to change in volume based upon said adjustment of said amount of said lysing agent;
   establishing an estimated measurement point in time which lies between boundaries of about one-third and about two-thirds of the period between said estimated adjusted first point in time and said estimated adjusted second point in time;
   introducing said adjusted amount of said lysing agent into said second control sample;
   determining size distributions for each of said first and second types of white blood cells in said at least one test sample at approximately said estimated measurement point in time; and forming an adjusted comparison of said size distribution of at least one of said first and second types of white blood cells from said at least one test sample taken at said estimated measurement point in time with said size distribution of said at least one of said first and second types of white blood cells from said second control sample; and whereby said positive diagnosis is indicated where the results of said adjusted comparison indicates a difference in said size distribution of said at least one type of white blood cell in said second control sample and in said at least one test sample by more than said predetermined amount.

8. The method of claim 7, wherein the control sample includes at least a third control sample, and the method further comprises the steps of:

introducing said adjusted amount of said lysing agent to said third control sample after said step of establishing said estimated measurement point in time;

doublechecking that said estimated measurement point in time actually lies between boundaries of about one-third and about two thirds of the difference between the time at which lysis occurs in said third control sample after introduction of said adjusted amount of said lysing agent to said third control sample and the time at which a change in the size distribution of at least one of said first and second types of white blood cells occurs; and if said estimated measurement point in time does not fall within said boundaries, further adjusting said adjusted amount of said lysing agent to be introduced into said at least one test sample, until said estimated measurement point in time does fall within said boundaries.

9. The method of claim 7, wherein said adjustment of said amount of said lysing agent is performed so that said estimated measurement point in time falls within a predetermined range.

10. The method of claim 9, wherein the control sample includes at least a third control sample, and the method further comprises the steps of:

introducing said adjusted amount of said lysing agent to said third control sample after said step of establishing said estimated measurement point in time;

doublechecking that said estimated measurement point in time actually lies between said predetermined range; and if said estimated measurement point in time does not lie within said predetermined range, further adjusting said adjusted amount of said lysing agent to be introduced into said at least one test sample, until said estimated measurement point in time does lie within said predetermined range.

11. The method of claim 9, wherein said method is performed with equipment having a known cycle for performing the method, and said predetermined range is selected so that said step of determining said size distribution of said at least one type of white blood cells in said at least one test sample falls at a predetermined point in said cycle.

12. The method of claim 1, further comprising the step of introducing a non-reactive substance into said control sample prior to said step of determining size distributions of said first and second types of white blood cells in said control sample.

13. The method of claim 1, further comprising the step of incubating said test sample after said introduction of said suspected reactant and prior to said comparison.

14. The method of claim 1 further comprising the step of:
separating the red blood cells from the white blood cells before said determination of size distributions of said first and second types of white blood cells.

15. A method for diagnosing whether a subject is sensitive to a reactant associated with a specific malady, the method comprising the steps of:

separating a sample of the subject's blood into a control sample and at least one test sample, said sample having at least red blood cells, a first type of white blood cells and a second type of white blood cells;

introducing a suspected reactant, associated with a specific malady, to said at least one test sample;

introducing a first lysing agent to said control sample;

determining size distributions for each of said first and second types of white blood cells in said control sample after a first point in time at which lysis of said red blood cells has reached a predetermined point and before a second point in time at which at least one of said first or second types of white blood cells in said control sample begin to change in volume;

introducing a second lysing agent to said at least one test sample;

determining size distributions for each of said first and second types of white blood cells in said at least one test sample after said first point in time and before said second point in time;

comparing said size distribution of at least one of said first and second types of white blood cells from said at least one test sample with said size distribution of said at least one of said first and second types of white blood cells from said control sample; and determining a positive diagnosis where the results of said comparison indicates a difference in said size distribution of said at least one type of white blood cell in said control sample and in said at least one test sample by more than a predetermined amount.

16. The method of claim 15, further comprising the step of:
monitoring lysis of said red blood cells in said control sample due to said introduction of said first lysing agent to said control sample, to thereby establish said first point in time.

17. The method of claim 15, wherein said first and second lysing agents are the same.

18. The method of claim 15, wherein at least one of said first and second lysing agents is saponin.

19. A method for diagnosing whether a subject is sensitive to a reactant associated with a specific malady, the method comprising the steps of:

separating a sample of the subject's blood into a control sample and at least one test sample, said sample having at least red blood cells, a first type of white blood cells and a second type of white blood cells;

introducing a first lysing agent to said control sample;

monitoring lysis of said red blood cells in said control sample due to said introduction of said first lysing agent to said control sample, to thereby establish a first point in time after said introduction of said first lysing agent into said control sample at which a predetermined amount of the red blood cells in the control sample are lysed, and a second point in time after said introduction of said first lysing agent into said control sample at which at least one of said first and second types of white blood cells in said control sample begins to change in volume;

determining size distributions for each of said first and second types of white blood cells in said control sample after said first point in time and before said second point in time;

introducing a suspected reactant, associated with a specific malady, to said at least one test sample;

introducing a second lysing agent to said at least one test sample;

determining size distributions for each of said first and second types of white blood cells in said at least one test sample after said first point in time and before said second point in time measured from the introduction of said second lysing agent to said at least one test sample;

comparing said size distribution of at least one of said first and second types of white blood cells from said at least one test sample with said size distribution of said at least one of said first and second types of white blood cells from said control sample; and determining a positive diagnosis where the results of said comparison indicates a difference in said size distribution of said at least one type of white blood cell in said control sample and in said at least one test sample by more than a predetermined amount.

20. A method for diagnosing whether a subject is sensitive to a reactant associated with a specific malady, comprising the steps of:

separating a sample of the subject's blood into a control sample and at least one test sample, said sample having at least red blood cells, and at least a first and a second type of white blood cell selected from the group consisting of the following types of white blood cells: basophils, eosinophils, neutrophils, monocytes and lymphocytes;

introducing a first lysing agent to said control sample;

measuring a first point in time after said introduction of said first lysing agent into said control sample at which substantially all of said red blood cells in said control sample are lysed;

measuring a second point in time after said introduction of said first lysing agent into said control sample at which at least one of said first and second types of white blood cells in said control sample begin to change in volume;

determining size distributions for each of said first and second types of white blood cells in said control sample after said first point in time and before said second point in time;

introducing a suspected reactant, associated with a specific malady, to said at least one test sample;

introducing a second lysing agent to said at least one test sample;

determining size distributions for each of said first and second types of white blood cells in said at least one test sample after said first point in time and before said second point in time, measured from the introduction of said second lysing agent to said at least one test sample;

comparing said size distributions of said first type of white blood cells in said at least one test sample after introduction of said suspected reactant to said test sample with said size distribution of said first type of white blood cells from said control sample;

comparing said size distributions of said second type of white blood cells in said at least one test sample after introduction of said suspected reactant to said test sample with said size distribution of said second type of white blood cells from said control sample; and determining a positive diagnosis where the results of at least one of said comparisons indicates a difference in said size distribution of at least one type of white blood cell in said control sample and in said at least one test sample by more than a predetermined amount.

21. A method for diagnosing whether a subject is sensitive to a reactant associated with a specific malady using an apparatus having a known cycle, the method comprising the steps of:

separating a sample of the subject's blood into at least first and second control samples and at least one test sample, said sample of the subject's blood having at least red blood cells, and at least a first and a second type of white blood cell selected from the group consisting of the following types of white blood cells: basophils, eosinophils, neutrophils, monocytes and lymphocytes;

introducing a first amount of a lysing agent to said first control sample;

identifying a first point in time after said introduction of said first lysing agent into said first control sample at which a predetermined amount of the red blood cells in said first control sample are lysed;

identifying a second point in time after said introduction of said first lysing agent into said first control sample at which at least one of said first and second types of white blood cells in said control sample begins to change in volume;

establishing a first measurement period having boundaries between about one-third and about two-thirds of the period between said first point in time and said second point in time;

determining if said measurement period includes a preferred measurement period which falls at a predetermined point in the cycle of the apparatus, and, if it does not, then establishing a second amount of lysing agent, different from said first amount of lysing agent, so that it is estimated that a second measurement period, different from said first measurement period due to said change from said first amount of lysing agent to said second amount of lysing agent, will fall within said preferred measurement period;

introducing said second amount of lysing agent to said second control sample;

determining size distributions for each of said first and second types of white blood cells in said second control sample during said second measurement period in said second control sample;

introducing a suspected reactant, associated with a specific malady, to said at least one test sample;

introducing said second amount of lysing agent to said at least one test sample;

determining size distributions for each of said first and second types of white blood cells in said at least one test sample during said second measurement period in said at least one test sample;

comparing said size distributions of said first type of white blood cells in said at least one test sample with said size distribution of said first type of white blood cells in said second control sample;

comparing said size distribution of said second type of which blood cells in said at least one test sample with said size distribution of said second type of blood cells in said second control sample; and determining a positive diagnosis where the results of at least one of said comparisons indicates a difference in said size distribution of at least one type of white blood cell in said second control sample and in said at least one test sample by more than a predetermined amount.

\* \* \* \* \*